United States Patent [19]
Royet et al.

[11] Patent Number: 5,482,924
[45] Date of Patent: Jan. 9, 1996

[54] PROTEINACEOUS COMPOSITIONS HAVING AN ACTIVITY ON ERYTHROPOIESIS

[75] Inventors: Julien Royet, Caluire; Sylvie Arnaud; Guy Mouchiroud, both of Villeurbanne; Jean P. Blanchet, Caluire, all of France

[73] Assignee: Centre National de La Recherche, Paris, France

[21] Appl. No.: 987,604

[22] Filed: Dec. 9, 1992

Related U.S. Application Data

[63] Continuation of Ser. No. 695,733, May 6, 1991, abandoned.

[51] Int. Cl.⁶ .......................... A61K 38/16; C07K 1/16; C07K 1/30; C07K 14/47
[52] U.S. Cl. ................... 514/8; 514/21; 514/814; 530/350; 530/395; 530/415; 530/416; 530/417; 530/420
[58] Field of Search .................. 514/8, 21, 814; 424/558, 577; 530/350, 395, 415, 416, 417, 420

[56] References Cited

U.S. PATENT DOCUMENTS

| | | | |
|---|---|---|---|
| 4,894,440 | 1/1990 | Rosenberg | 530/418 |
| 4,987,121 | 1/1991 | Baertschi et al. | 514/8 |
| 5,032,507 | 7/1991 | Yu et al. | 424/93 |

FOREIGN PATENT DOCUMENTS 8101367  5/1981  WIPO.

OTHER PUBLICATIONS

Kohama et al "A Burst–Promoting Activity Derived from the Huamn Bone Marrow Stromal Cell Line Kμ–102 . . ." *Exp. Haematol.* 16:603–608 (1988).
Royet et al, *Blood* 76(10): 1965–1971, Nov. 15, 1990.
Oddos et al, *J. Cell. Physiol.* 133:72–78, 1987.
Porter et al, *Blood* 59(6): 1207–1212, Jun. 1982.
Clark et al, *Science* 236: 1229–1237, Jun. 5, 1987.
Kohama et al, *Exp. Hematol* 16(7): 603–608, 1988, abstracted in *Biol. Abstr.* 86(8): AB–527, Ref. No. 80836, Oct. 1988.
Eliason et al, *Cell Tissue Kinet.* 16(1): 65–76, 1983, abstracted in *Biol. Abstr.* 76(1): 75, Ref No 673, 1983.

*Primary Examiner*—Stephen G. Walsh
*Attorney, Agent, or Firm*—Omri M. Behr; Matthew J. McDonald

[57] ABSTRACT

The invention relates to proteinaceous compositions capable of modulating the development of erythroid progenitors such as obtainable from a biological material selected from bone marrow culture supernatants, or kidney cell lysates by contacting said biological material with a specific ligand for the proteinaceous compositions, desorbing said proteinaceous compositions and recovering same by elution. Said compositions are useful in therapeutics.

9 Claims, 4 Drawing Sheets

PROTEINACEOUS COMPOSITIONS HAVING AN ACTIVITY ON ERYTHROPOIESIS

This application is a continuation, of application Ser. No. 07/695,733, filed May 6, 1991, which is now abandoned.

FIELD OF THE INVENTION

The invention relates to protein compositions and fractions thereof having biological properties, particularly the ability of stimulating erythropoiesis.

The invention also relates to a process for obtaining said products and to their use as active principles in drugs.

BACKGROUND OF THE INVENTION

Red blood cell production in vetebrates results from the proliferation and differentiation of a sequence of progenitors arising from multipotential hematopoietic stem cells. Two erythropoeitic progenitor populations have been well characterized in the mouse: 1) the Burst-Forming Unit-Erythroid (BFU-E) population containing immature progenitors giving rise, within 7 days, to large multicentric erythroid colonies, in semi-solid cultures, called bursts; 2) the Colony-Forming Unit-Erythroid (CFU-E) population which is composed of more mature progenitors forming colonies of 8 to 64 red cells within 48 hours.

Two kinds of regulators control the differentiation of these erythropoietic progenitors. Erythropoietin (Epo), a hormone synthetized by the kidney, is required for CFU-E proliferation and differentiation whereas Burst-Promoting Activity (BPA) induces the development of BFU-E. This activity is shared by Interleukin 3 (IL3) stem cell factor, Granulocyte-Macrophage Colony-Stimulating Factor (GM-CSF) and Interleukin 4, (IL4).

Whereas Epo and IL3 are the major erythroid growth factors in vitro, other factors can also modulate the development of erythroid progenitors.

Patients suffering from chronic renal failure or anephric patients develop severe anemia and require regular blood transfusions with risk of hepatitis, iron overload and sensitization to major or minor histocompatibility antigens. The recent availability of recombinant human erythropoietin has allowed treatment of these patients with this hormone with significant results. It was however noticed that the large quantities of Epo given to the patients were less effective than the endogeneous Epo produced in those patients after renal transplantation.

SUMMARY OF THE INVENTION

The inventors have found that an erythropoietic activity is expressed by specific proteins and is active in vivo being thus able to be used for treating said patients together with repeated injections of Epo.

It is then an object of the invention to provide proteins and fractions containing them.

It is a further object of the invention to provide a process for preparing said products.

It is still another object of the invention to provide products containing active principles useful for making drugs.

The proteinaceous compositions of the invention which stimulate erythropoiesis, comprise proteins having in particular, the following properties:

they are precipitable by an aqueous solution of ammonium sulphate between from 30 to about 40% (vol.), they have an affinity for a lectin, suitably Concanavalin A at pH 7.4, in a phosphate buffered saline (PBS), they cannot be fixed on an anion exchange resin using ethanolamine at pH 9.5, 20 mM, they stimulate in vivo mature erythroid burst-forming-unit proliferation, especially in the spleen of animals, they stimulate in vivo colony forming unit erythroid progenitors, especially in the spleen of animals.

According to another aspect, the compositions of the invention are obtainable by a process which comprises treating a material having an erythropoiesis stimulating activity to selectively recover at least the major part of the proteins having said stimulating activity, said treatment comprising, suitably, the steps of:

a) contacting said material with a ligand capable of selectively adsorbing the proteins having said activity, b) desorbing said proteins, c) recovering the selected proteins from the eluate.

The products recovered from the above mentioned process may be subject to one or more steps in order to selectively separate the desired proteins having in vivo activity as erythropoietic factor.

Said separation is advantageously carried out by fractionating the eluted products according to their molecular weight and/or their isoelectric point, and recovering the desired fractions.

The preferred fractions of the invention are obtained by gel filtration or ion exchange and have a molecular weight (MW) of about 100 kDa.

Other useful fractions also obtained by gel filtration have a MW of about 35 kDa.

Still other useful fractions have a MW of about 15 kDa.

According to the invention there is also provided a process for obtaining said compositions and fractions.

Said process comprises treating a material having an erythropoiesis stimulating activity to selectively recover at least the major part of the proteins having said stimulating activity, said treatment advantageously comprising the steps of:

a) contacting said material with a ligand capable of selectively adsorbing the proteins having said activity, b) desorbing said proteins, c) recovering the selected proteins from the eluate.

DESCRIPTION OF THE PREFERRED EMBODIMENTS

The material having said activity is advantageously selected from the group comprising kidney cell lysate (Royet J. et al, Blood, vol. 76, p 1965–1971, 1990) or bone marrow cell culture supernatant (Oddos T, J. of cellular Physiology, vol. 133, p 72–78, 1987).

Contact step a is performed on said raw material, or preferably, with proteins precipitated therefrom.

For example, said raw material is treated with an aqueous solution of ammonium sulphate, suitably from about 30 to about 40% w/v, to selectively precipitate at least the major part of the desired proteins.

Before being contacted with the ligand, suitably a lectin, the precipitate is dissolved in a buffer at pH close to the neutrality, suitably from about 7 to 7.5, preferably of about 7.4.

Appropriate buffers include isotonic saline solution such as PBS.

The separation and the recovery of the fractions which contain the desired proteins is suitably carried out by chromatography in a column containing bound lectin.

Satisfactory results are obtained by using a lectin having an affinity for glycoproteins. Such lectins include concanavalin A which will be used linked to a gel of agarose such as the one commercialized under the trademark Sepharose®.

The column is equilibrated with a buffer such as above defined.

The products devoid of or having a low affinity for the lectins are eliminated by rinsing with a buffer suitably of the same type as the one used for equilibrating the column.

A preferred mode of recovering the lectin retained or adsorbed products, having a stimulating activity on erythropoiesis comprises desorbing said products by elution.

The eluent will be chosen among those which do not interfere with the subsequent recovery steps of the proteins contained in said compositions.

Appropriate aqueous eluents comprise solutions of saccharides capable of challenging the immobilized lectin and the glycoprotein fixed thereon.

Suitable saccharides comprise α-methyl glucopyranoside. After elutions of the proteins having a lectin affinity, an ammonium sulphate precipitation is advantageously carried out on the eluate to recover the proteins by centrifugation.

In order to have purified protein fractions, one or several fractionation steps are then performed.

Ion exchange chromatography, suitably anion exchange chromatography with Mono Q column from Pharmacia, or any other method which would yield similar results, will then be used. The proteinaceous compositions which stimulate erythropoiesis have no fixation on an anion exchange resin using ethanolamine at pH 9.5, 20 mM.

In order to separate specific fractions, a solution of the above fractions is deposited on a reverse phase column. Active fractions are collected.

By gel filtration of the proteins eluted from the ion exchange chromatography column, several peaks of activity are detected corresponding to fractions having molecular weights of about 100, 35 and 15 kDa.

According to one embodiment, the material used in above step a is the supernatant of bone marrow cell culture whose activity on erythropoiesis is stimulated by erythropoietin.

Said cell culture is such as obtained by a method comprising:

culturing up to the establishment of an adherent cell monolayer, in a medium made of modified Dulbecco's Medium containing 15% horse serum, 5% foetal bovine serum, 0.4 mg/ml human transferrin, $10^{-6}$M hydrocortison and antibiotic, removing the non adherent cells, immortalizing the nutritious adherent cells, which produce active supernatant when stimulated by erythropoietin, cloning the immortalized transformed cells and, isolating the clones having a stimulating effect on the proliferation of BFU-E, and recovering the supernatants.

The immortalization step is advantageously carried out by transfecting the cells with a vector bearing a proto-oncogen or any other gene confering immortalization and a selection gene.

It is convenient to use, according to the usual transfection methods, a proto-oncogen or an oncogen.

Examples of proto-oncogen include human c-fos proto-oncogen- or antigen T of SV40.

The vector will preferably be a plasmid, a retrovirus, suitably Moloney virus.

The marker is chosen so as to easily detect cell transfection.

Appropriate markers include an antibiotic resistance gene. The cells showing a resistance to the antibiotic are subcloned.

The bone marrow cells are of human or other mammal origin.

A mouse bone marrow cell line was deposited at the Collection Nationale de Culture de Microorganismes (CNCM) Institut Pasteur, 28, we Dr. Roux, 75124 ledex Paris 15, France under n. I.1062 on Mar. 20, 1991.

The bone marrow cell lines such as above defined, more particularly said deposited cell line, are part of the invention.

Such cell lines are characterized by the fact they are formed from adherent cells, having a fibroblastic behavior, expressing type I and type III collagen, but not type IV collagen, which confers on them fibroblast properties. The doubling time of the cells is of about 48 hours. Particularly satisfactory conditions for growing include the use of horse serum.

According to an aspect of great interest, the immortalized cell lines of the invention constitutively express said stimulating activity on erythropoieisis in the supernatant, the synthesis of the erythropoietic factor not being increased during incubation of the cells in the presence of erythropoietin.

The bone marrow cell line supernatants of the invention are characterized in that they are capable to stimulate BFU-E proliferation at concentration of about 1%, more particularly the formation of erythropoietic bursts of reduced size.

According to another embodiment, the material used in step a of the process of the invention is obtained from kidney cell lysates.

The protein compositions and fractions of the invention are endowed with biological activities enabling them to stimulate erythropoiesis.

In vivo assays have demonstrated the presence of strong activity of their erythropoietic factor. Said activity will be illustrated hereinafter by results obtained on mice.

A salt precipitate (ammonium sulphate 40% final concentration) of mouse kidney cell lysate was injected to C57 BL/6 mice. The kidney cell lysates were obtained from mice rendered anemic by one intra-peritoneal injection of phenylhydrazine (10 mg/kg) the day before harvesting kidneys.

The dosage was equivalent to the cells in half a kidney per injection. Injections were repeated during 5 consecutive days. An important increase in the CFU-E number was observed in the spleen.

The number of the erythroid progenitors (CFU-E) was increased of about 4 to 5 times, a maximum being noticed after 3–4 days of treatment, compared to control animal injected with PBS.

The number of BFU.E in the spleen is increased 2 to 3 times after a 4 day treatment.

The erythropoietic factor of the kidney cell lysate which is responsible for the activity thus appears to be endowed with high stimulative properties.

The compositions and purified fractions of the invention are free of toxicity.

The compositions and fractions of the invention are thus particularly suitable for stimulating erythropoiesis in man or animal.

The invention further relates to pharmaceutical preparations which contain protein fractions having a high stimulating activity on erythropoiesis as measured according to the methods given in the examples hereinafter.

It more particularly relates to pharmaceutical preparations devoid of pyrogenic substances, containing an effective amount of a compositions as above defined or a fraction thereof, in association with pharmaceutical excipients.

Particularly, it concerns the preparations in which the pharmaceutical vehicle is suitable for administration by the intraperitoneal or sub-cutaneous route.

Corresponding dosage forms are sterile or sterilizable solutions. Such solutions preferably contain 50 to 5000 μg/ml of active principle, preferably 500 μg/ml.

The invention also relates to pharmaceutical preparations containing said fractions or compositions in association with another active principle, for example erythropoietin.

Erythropoietin (10 000 u/ml) will be used at dosis of about 500 u/kg body weight.

The pharmaceutical preparations of the invention are particularly adapted to the treatment of patients suffering form chronic renal deficiencies, or anephric patients developing severe anemia.

The posology for a patient having chronic renal deficiency will comprise for example the administration to the patient of 5 to 50 μg/kg 2 or 3 times weekly.

Said posology is indicated for the sole purpose of illustrating the invention, the indicated doses should naturally be adjusted for each patient according to the results of blood analyses, the state of health.

It is also an object of the invention to provide a method of treatment of anemia or erythropoiesis disorders such as observed with patients having chronic renal failures, said method comprising administering to said patients a pharmaceutical composition as above-defined.

The invention also relates to the use of the compositions and fractions as biological reactants which are of interest for studying effect on erythroid progenitor proliferation in comparative studies.

The invention will be illustrated hereinafter with examples disclosing the obtention of compounds of the invention. Said examples are given for the sake of further illustrating the invention, yet in a non limitative manner.

BRIEF DESCRIPTION OF THE DRAWINGS

It will be referred therein to FIGS. 1 to 4.

EXAMPLES

EXAMPLE 1

Bone marrow cell cultures:

$2\times10^6$ cells of mouse bone marrow were seeded in dishes of 35 mm diameter, in a modified Dulbecco's medium (IMDM) supplemented with (final concentration): horse serum (15%), foetal calf serum (5%), Fe saturated transferrine (0.4 mg/ml) hydrocortisone ($10^{-6}$), penicillin 100 u/ml, streptomycin (0.1 mg/ml).

An adherent cell monolayer was formed.

After 15 days, the non adherent cells were removed and fresh bone marrow was re-seeded in the presence of 0.1 U/ml of erythropoietin (Epo).

Figure 1:
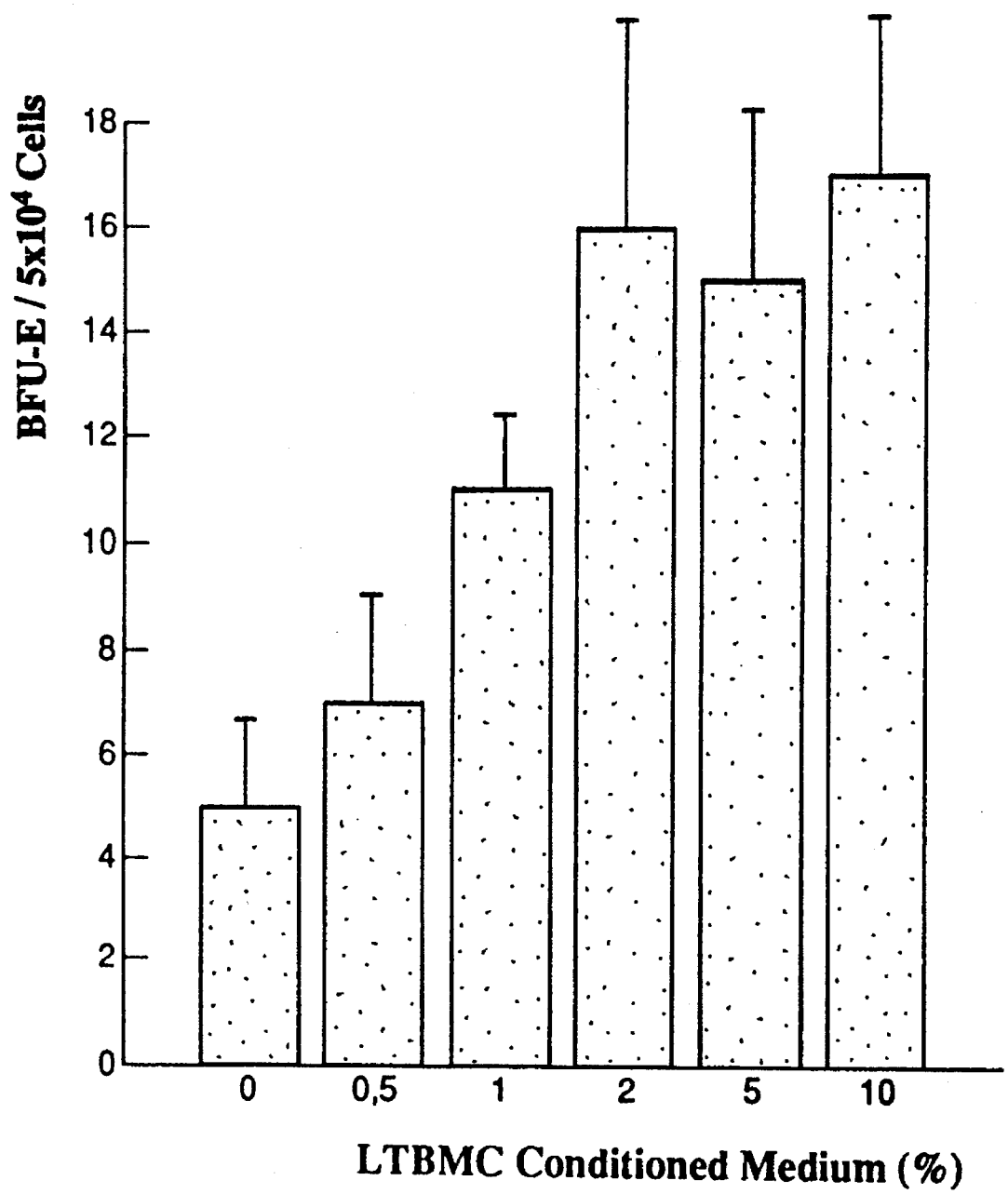
FIGS. 1 and 2 represent the formations of BFU-E under various culture conditions.

The activity of supernatants of long term cultures is reported on FIG. 1 which gives the number of bursts in the culture as a function of conditioned medium concentration %.

A stimulation optimum is obtained at 2%.

The adherent cells were transfected with a retroviral vector bearing human C-fos proto-oncogen c-CDNA and the neomycin gene. The transfected cells were selected by using G418. The resistant cells were sub-cloned and the supernatant assayed on mouse bone marrow cells to determine their stimulating effect on the proliferation of BFU-E.

Figure 2:
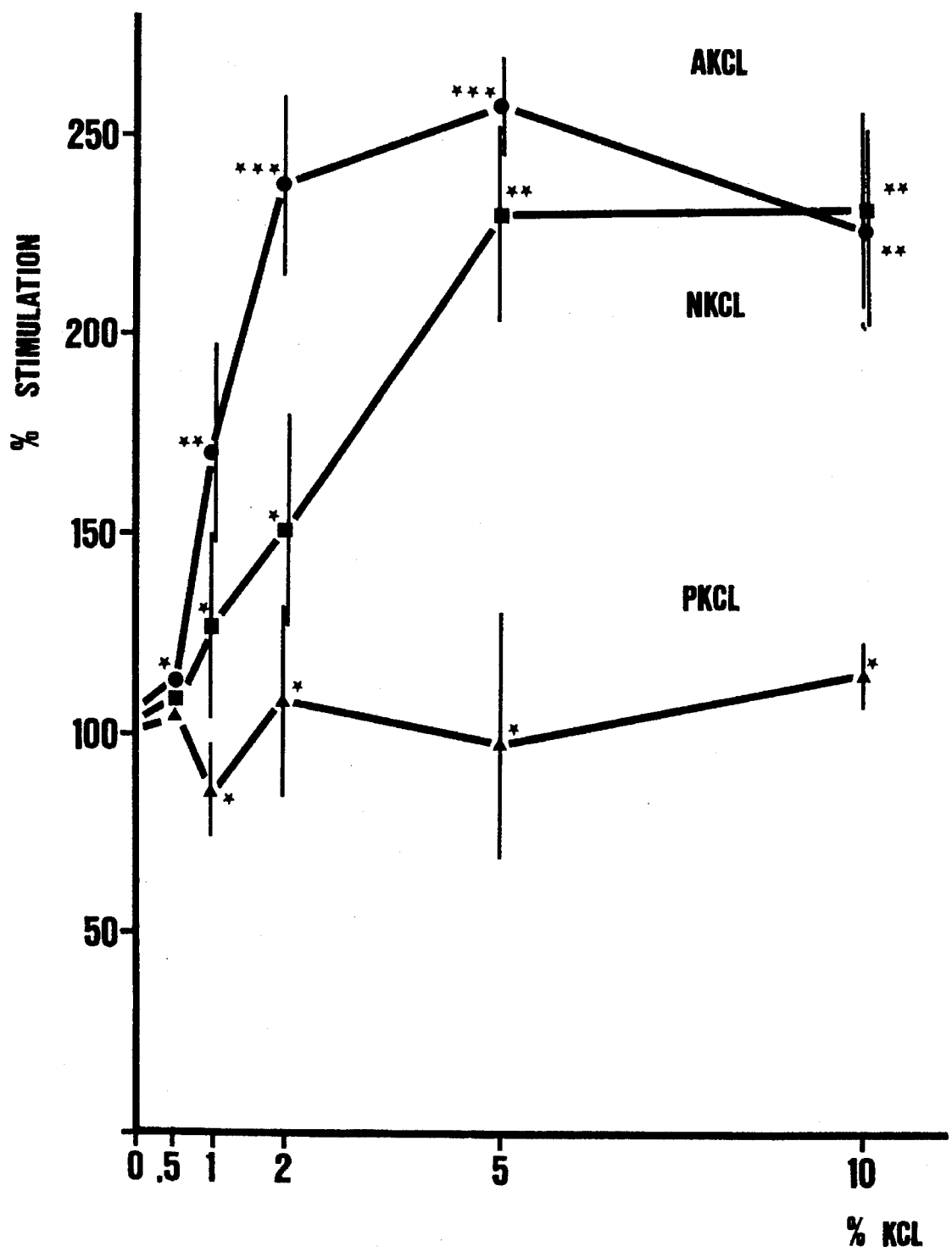

FIG. 2 shows the variation of BFU-E$5\times10^4$ cells with increased amounts of N cell conditioned medium (%).

EXAMPLE 2

Protein fractions obtained from bone marrow cell culture supernatant:

An aqueous solution of ammonium sulphate from about 30 to 40% w/v was added to the supernatant of example 1 in order to precipitate the desired proteins.

The whole of the activity was found in the precipitated proteins (about 5% of the total amount of proteins).

The precipitate was centrifugated, dissolved into PBS and the solution was deposited on an affinity column of concanavalin A fixed on Sepharose.

The column was eluted with PBS and aqueous α-methyl glucopyranoside 0.5 N.

Ammonium sulphate (90%) w/v is added to the eluate to precipitate the proteins. After centrifugation, the plug was recovered, dissolved in a phosphate buffer 20 mM, pH 11.8 and the solution was deposited on an ion exchange column.

The active proteins were not retained and the recovered eluate treated by ammonium sulphate (90% vol.) to precipitate the desired proteins.

Said proteins were dissolved in trifluoroacetic acid and the solution was deposited on a reverse phase column.

By gel filtration 3 peaks corresponding to active proteins are separated, having a MW of about 100, 35 and 15 kDa, respectively.

EXAMPLE 3

Kidney cell lysates

Kidneys were removed from anemic, normal or polycythemic mice and perfused with Phosphate Buffered Saline (PBS) supplemented with 2% Fetal Bovine Serum (FBS, Flow Labs, Roockville, Md.). They were fragmented using scissors and passed through a syringe provided with a 0.9 mm diameter needle. The suspensions were then filtered through nylon mesh (125 μm). Cells were washed twice in PBS, enumerated, resuspended at $2.5\times10^7$ cells/ml in a Tris-HCl 10 mM pH 7.4 hypotonic buffer supplemented with NH$_4$Cl 25 mM, MgCl$_2$ 10 mM, 2-mercaptoethanol (0.25 mM and Tween 80, 0.01% and frozen at −80° C. Before use, samples were thawed and centrifuged at 8,500 g for 5 mn. Supernatants were harvested, sterilized by filtration and tested in culture.

EXAMPLE 4

In vitro assay of erythroid progenitors

Semi-solid cultures of CFU-E were established in IMDM supplemented with 30% FBS, 1% deionized Bovine Serum Albumin (BSA) (Boehringer), $7.5\times10^{-5}$ M 2-Me, 0.2 U/ml porcine Epo and 0.8% methylcellulose (Fluka A. G., Buchs, Switzerland). Cells were plated at a final concentration of $2\times10^4$ cells/ml in a volume of 100 µl into wells of microtitration plates (Costar, Cambridge, Mass.). Cultures were incubated at 37° C. in a water-saturated atmosphere containing 2.5% $CO_2$, for 2 days. Colonies of more than 8 cells derived from CFU-E were enumerated after benzidine staining using an inverted microscope.

Figure 3A:
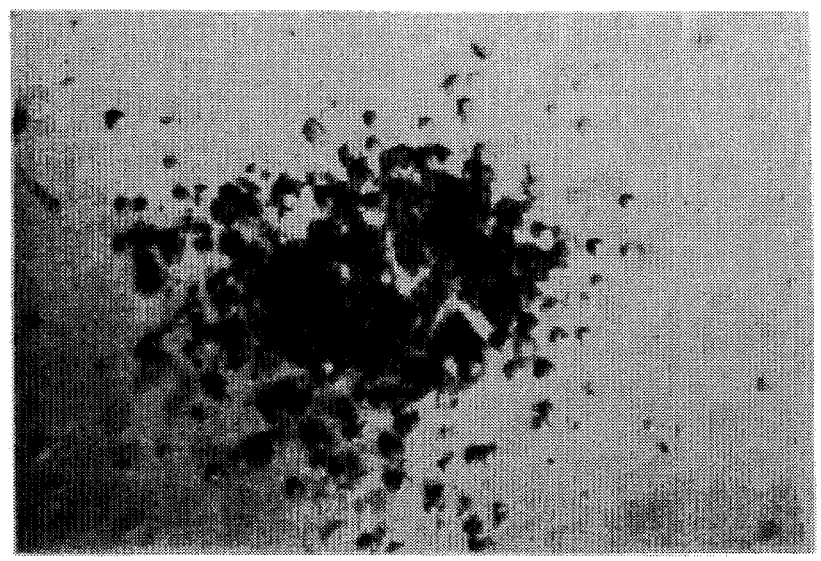
FIG. 3 is a micrograph of iBFU-E (A) magnification (×50) and mBFU-E (B) magnification (×100) and FIG. 4 gives results of comparative studies.
Figure 3B:
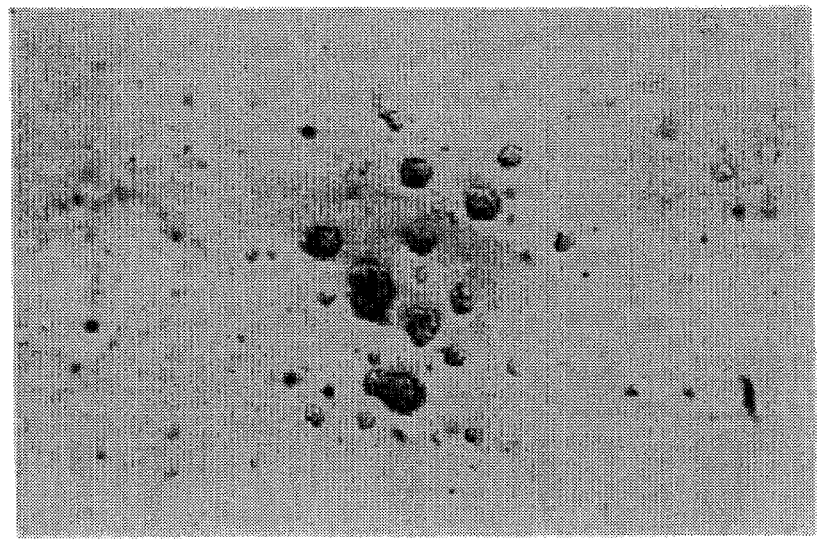

Semi-solid cultures of BFU-E were made in IMDM supplemented with 20% FBS, 1% deionized BSA, $7.5\times10^{-5}$ M 2-Me, $4.5\times10^{-5}$ M hemin (Sigma) and 0.8% methylcellulose. Porcine Epo or rhEpo (0.5 U/ml) was added in the presence of WEHI-3 conditioned medium or purified mIL3 as indicated and kidney cell lysate concentrations as specified below. Both sources of Epo and IL3 gave similar results. Cells were plated at a final concentration of $2\times10^4$ cells/ml in a volume of 500 µl into 16 mm diameter wells. Cultures were incubated at 37° C. in a water-saturated atmosphere containing 5% $CO_2$ for 7 days. Bursts were counted without staining: small (less than 15 sub-colonies) and large (over 15 subcolonies) bursts were discriminated and were respectively ascribed to the development of mature BFU-E (mBFU-E) or immature BFU-E (iBFU-E) (FIG. 3).

EXAMPLE 5

Long term bone marrow cell cultures (LTBMC)

$10^6$ C57BL/6 bone marrow cells were placed in IMDM containing 15% selected horse serum (Biosys), 5% FBS, 0.4 mg/ml human transferrin (Boehringer), $10^{-6}$ hydrocortisone (Sigma) and antibiotics. They were allowed to adhere for 1 week. The culture medium was removed and fresh C57BL/6 bone marrow cells were then added in fresh medium. One week later, porcine Epo (0.1 U/ml) with or without 5% of Anemic Kidney Cell Lysate was added. Medium was half-changed three times a week. At different times, all the cells were harvested, enumerated and placed in cultures for detection of CFU-E.

EXAMPLE 6

Effect of kidney cell lysates

1. Kidney cell lysates increase the number of small bursts.

It is well known that bone marrow cells plated in the presence of IL3 and Epo form pure erythroid bursts. These bursts are heterogeneous in size, ranging from a few to a hundred sub-colonies (FIG. 3). This size variability is thought to reflect the maturation step of the progenitors giving rise to the bursts.

In the presence of Epo only, the number of bursts increased with the Epo concentration and reached a plateau for 0.5 U/mL; this Epo concentration was used in all subsequent experiments. Moreover, it was observed that only small bursts develop in these conditions. Addition of 5% AKCL (anemic kidney cell lysate) increases significantly the number of bursts to a plateau of about twice the number of bursts counted in the presence of Epo only. Only small bursts of less than 15 sub-colonies were observed in these cultures. The addition of a saturating mIL 3 concentration (50 U/mL) to cultures also increased the number of bursts to values similar to those reached with AKCL. However, since small and large bursts develop in the cultures containing mIL3, said results show that AKCL stimulates mature BFU-E to a greater extent thant mIL3.

2. Activity of kidney cell lysates as a function of the erythropoietic status of the donors.

Figure 4:
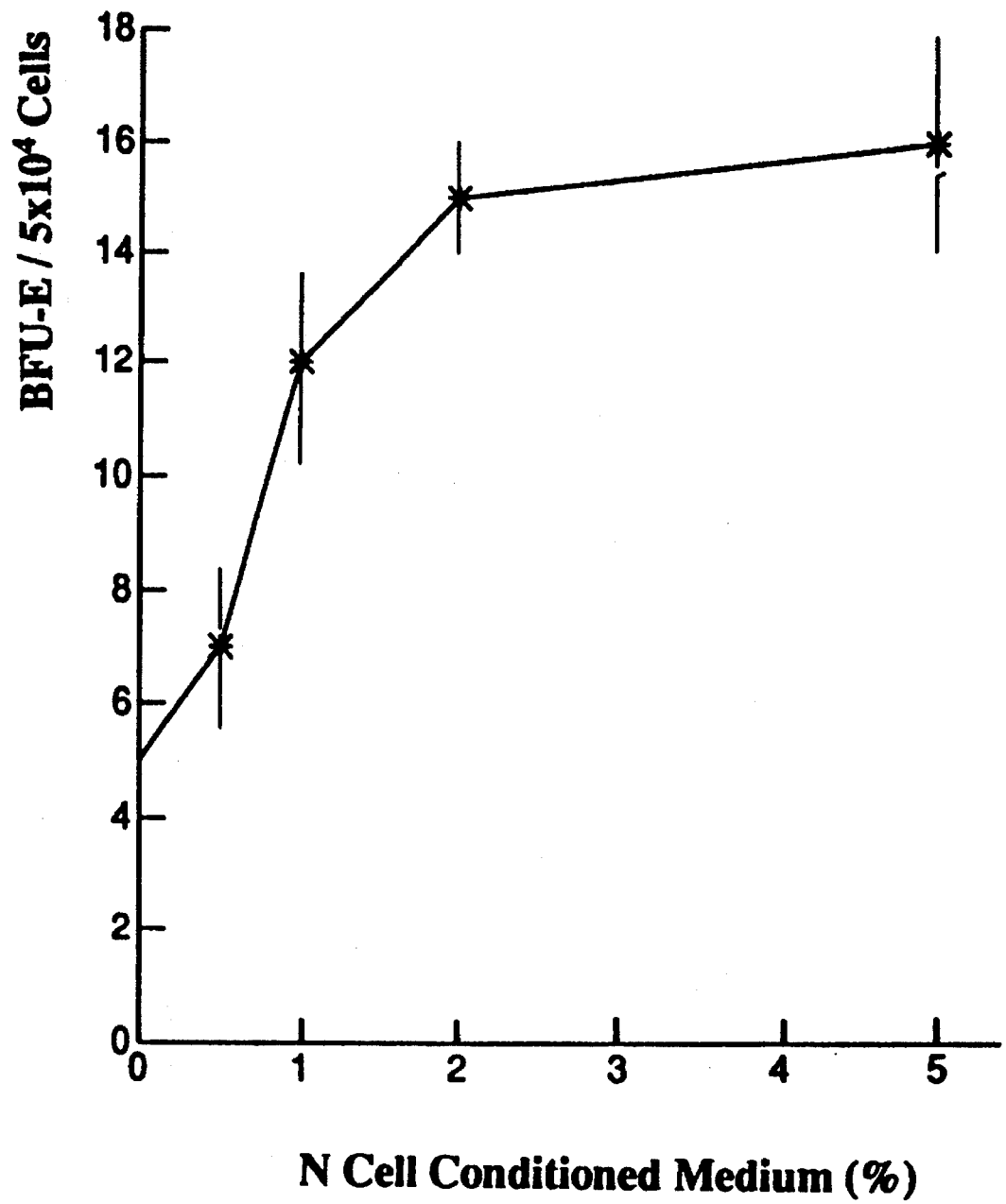

The dose-response curves for extracts of kidneys from anemic, normal and polycythemic mice are shown in FIG. 4. A significant increase in the number of small bursts was observed when normal kidney cell lysates were introduced at 5 to 10% into the cultures (p<0.05). At lower concentrations, NKCL (normal kidney cell lysates) was without effect on BFU-E development. In contrast, only 1% of AKCL was necessary to obtain a significant increase (p<0.5), and a maximal stimulation was obtained with 2% of AKCL (p<0.02). A similar increase in AKCL prepared from mice rendered anemic by bleeding was also seen (not shown).

The addition of polycythemic kidney cell lysate (PKCL) did not increase the number of small bursts, as compared to cultures containing only Epo (p<0.05). Even when used at 10%, PKCL was unable to stimulate mBFU-E development in culture.

Bursts obtained in cultures established in the presence of AKCL and Epo are rather homogeneous in size, ranging from 4 to 15 sub-colonies. In contrast, cultures stimulated by IL3 and Epo also exhibit large bursts with more numerous and large sub-colonies and also large myeloid colonies. In addition it was observed that small bursts were hemoglobinized from the fifth or sixth days of the culture, while large hemoglobinized bursts were seen only after 7–8 days of cultures. For these reasons, it was assumed that small bursts develop from an erythroid progenitor (mature BFU-E:mBFU-E) intermediate between CFU-E and iBFU-E giving rise to large erythroid bursts (immature BFU-E:iBFU-E). The erythropoietic activity present in kidney cell lysates was therefore called Mature Burst Promoting Activity (MBPA)

When using extracts made from kidneys harvested from anemic, normal or polycythemic mice, the activity of these extracts were strictly correlated with the erythropoietic activities of the donors: low in polycythemic and high in anemic kidneys relative to the normals (FIG.4).

Thus, although both erythropoietic factors appear to be regulated in a similar manner, as a function of the erythropoietic status of the animal, erythropoietin production seems to be more stringently regulated an observation that would be related to the important role of this hormone in the day to day maintenance of the red cell count.

The total number of iBFU-E and mBFU-E was studied in the bone marrow and the spleen or polycythemic mice, whereas iBFU-E did not vary greatly, the total number of mBFU-E was highly increased at a time when kidney cell extracts became less active and then inactive. This kinetics could be ascribed either to the decrease of MBPA or to the absence of Epo. It was observed that CFU-E number in bone marrow of polycythemic mice decreased to a basal level within 4 days of treatment.

In contrast, no change in mBFU-E was observed at this time. These results suggest that the decrease in Epo levels in polycythemic mice mainly affects CFU-E number, whereas the later reduction in MBPA could result in the accumulation of mBFU-E. Moreover, it was shown that the mBFU-E which were accumulated in polycythemic mice were almost all MBPA-sensitive progenitors which need both Epo and MBPA to differentiate.

The data reported herein show that besides erythropoietin, another hematopoietic factor is produced by the kidney. Similar results were obtained with extracts of human and primate kidney cell.

We claim:

1. Proteinaceous compositions precipitated from bone marrow supernatant or kidney cell lysates which, in combination with erythropoietin, stimulate erythropoiesis said proteinaceous compositions comprising proteins having the following properties:

they have been precipitated from a biological material selected from the group consisting of the supernatant of a culture of the mouse bone marrow cell line deposited at the CNCM under number I.1062 on Mar. 20, 1991 and kidney cell lysates, by bringing said supernatant or lysates to a final aqueous ammonium sulphate concentration of about 30 to 40% (w/v), they are adsorbed by bound lectin having an affinity for glycoproteins in a phosphate buffer saline (PBS), pH 7.4, in vitro, they effect an increase in the number of small bursts having fifteen or fewer erythroid sub-colonies, and in vivo they stimulate mature erythroid burst-forming-unit proliferation, thus increasing the colony forming unit erythroid number.

2. The compositions according to claim 1 obtained by a process which comprises treating said bone marrow supernatant or kidney cell lysate having an erythropoiesis stimulating activity to selectively recover at least the major part of the proteins having said stimulating activity, said process comprising the steps of:

a) contacting an aqueous suspension of said precipitated proteins with a ligand capable of selectively adsorbing the proteins having said activity, b) desorbing said proteins from said ligand in an eluate, and c) recovering said proteins from the eluate by further precipitating said proteins.

3. The compositions according to claim 2, wherein a further step is performed on said proteins to obtain separate protein fractions, said step being a fractionation step selected from the group consisting of gel filtration and ion exchange.

4. The protein fractions obtained according to claim 3.

5. The fraction according to claim 4, having MW of about 100 kDa.

6. The fraction according to claim 4, having a MW of about 35 kDa.

7. The fraction according to claim 4, having a MW of about 15 kDa.

8. A process for further purifying the compositions of claim 1, comprising the steps of:

a) contacting an aqueous suspension of the precipitated proteinaceous composition of claim 1 with a bound lectin having affinity for glycoproteins, said lectin being capable of selectively adsorbing the proteins having an erythropoiesis stimulating activity, b) desorbing adsorbed proteins from said lectin in an eluate to provide an eluate containing said proteins, and c) recovering said proteins from the eluate by further precipitating said proteins.

9. A pharmaceutical preparation for erythropoiesis restoration comprising therapeutically effective amounts of erythropoietin and of a composition according to claim 2 in association with a pharmaceutical excipient.

* * * * *